United States Patent [19]

Rich

[11] Patent Number: 4,875,974

[45] Date of Patent: Oct. 24, 1989

[54] ABSORBENT VEGETABLE MATERIAL AND PROCESS FOR MAKING SAME

[75] Inventor: Thomas F. Rich, Cincinnati, Ohio

[73] Assignee: The Procter & Gamble Company, Cincinnati, Ohio

[21] Appl. No.: 146,059

[22] Filed: Jan. 20, 1988

Related U.S. Application Data

[63] Continuation of Ser. No. 522,873, Aug. 11, 1983, abandoned.

[51] Int. Cl.$^4$ .................................................. D21C 5/00
[52] U.S. Cl. ........................................ 162/10; 162/91; 162/99; 162/175; 162/178; 536/2; 536/128; 604/364; 604/374
[58] Field of Search ..................... 162/91, 99, 10, 11, 162/175, 178; 604/364, 374; 536/2, 128; 127/29, 34

[56] References Cited

U.S. PATENT DOCUMENTS

| | | | |
|---|---|---|---|
| 1,393,660 | 10/1921 | Beylik | 536/2 |
| 2,502,477 | 4/1950 | Owens | 536/2 |
| 4,143,172 | 3/1979 | Mitchell | 426/532 |

*Primary Examiner*—Peter Chin
*Attorney, Agent, or Firm*—Gary M. Sutter; Michael P. Brennan; Richard C. Witte

[57] ABSTRACT

An absorbent material derived from a vegetable material containing pectin.

9 Claims, 1 Drawing Sheet

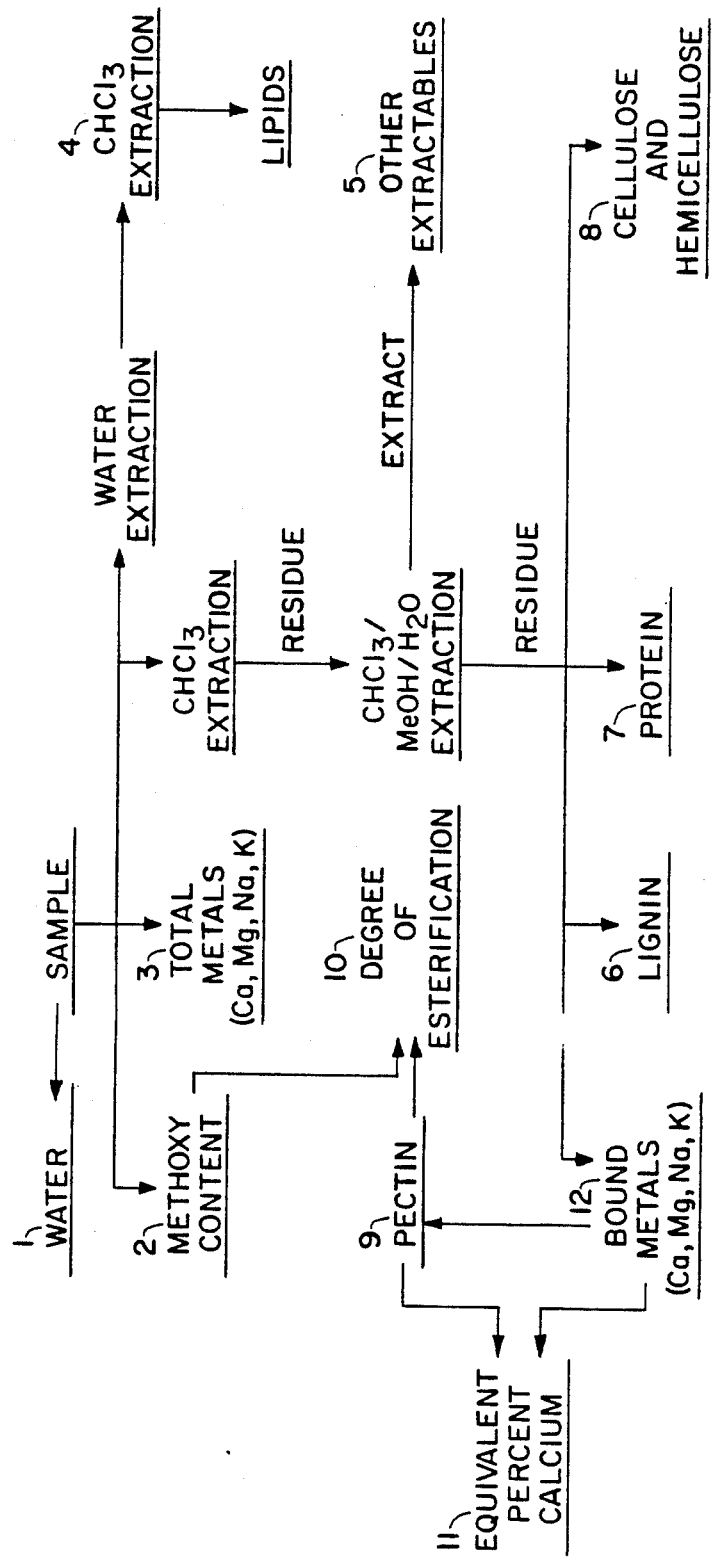

ABSORBENT VEGETABLE MATERIAL AND PROCESS FOR MAKING SAME

This is a continuation of application Ser. No. 522,873, filed On Aug. 11, 1983, now abandoned.

TECHNICAL FIELD

This invention relates to novel absorbent materials of vegetable origin, and the process for making such absorbent materials.

Disposable absorbent products (e.g. disposable diapers, sanitary napkins, and the like) generally contain absorbent webs of wood pulp fibers. Depending on the climate, it takes a tree from about 20 years to about 40 years to mature to a harvestable state. Consequently, to meet the demand for wood pulp fibers to be used in absorbent materials, vast areas of land are necessary for the growing of trees. As another consequence, even though wood pulp fibers are probably the most economical material for use in disposable absorbent products available today, substantial expenditures are being made in the harvesting and growing of the trees. There is therefore a continuing need for alternative, inexpensive absorbent materials, preferably from renewable resources.

It has now been discovered that certain pectin-containing agricultural by-products can be converted to highly absorbent materials, suitable for use in disposable absorbent products, via a relatively simple and inexpensive process. Typical examples of agricultural by-products suitable as raw materials for the absorbent materials of the present invention include the residue material from citrus juice processors and from sugar beet refineries. These materials are therefore abundantly available at low cost.

The pectin-containing agricultural residue material can be converted to a highly absorbent material by a process involving hydrolysis or partial hydrolysis of the pectin methyl esters present in waste materials; and subsequent washing and drying of the material. The absorbent properties of the materials may be further improved by subject them to a bleaching step. Such a bleaching step also improves the appearance of the product, thereby making it more acceptable for use in disposable absorbent products. The vegetable-derived absorbent materials typically have an absorbent capacity which is from 2 to 5 times that of conventional wood pulp fiber webs. These materials therefore offer an opportunity to reduce the bulk of absorbent products while maintaining their containment capacity.

It is therefore an object of this invention to provide an inexpensive absorbent material, suitable for use in disposable absorbent products. It is another object of this invention to provide a process for converting certain pectin-containing agricultural waste materials to the absorbent materials of this invention.

BACKGROUND OF THE INVENTION

The agricultural waste materials suitable as starting materials for the manufacturing of the absorbent materials of the present invention are being produced in large quantities. The waste material from citrus juice processors consisting of peels (i.e. albedo and flavedo) and rag, is generally processed to cattle feed by what has been termed the "lime de-watering process". This process comprises the steps of treating the waste with "lime" (calcium oxide, calcium hydroxide, or even calcium carbonate) to convert it from a slimy, unpressable condition to a watery, pressable condition; pressing the converted waste; and drying (see, for example, U.S. Pat. No. 2,147,521, issued Feb. 14, 1939 to Florida Citrus Exchange; U.S. Pat. No. 2,215,944, issued Sept. 24, 1943 to Vincente, U.S. Pat. No. 2,362,014, issued Nov. 7, 1944 to Citrus Processes, Inc.).

Relatively small quantities of citrus waste are used as a source of pectin, which can be used as a thickening agent in food products. Food thickening agents may also be prepared by comminuting citrus peel material, and lowering the degree of esterification of the pectic materials in the citrus peel by enzymatic or chemical treatment. This approach has been disclosed in U.S. Pat. No. 3,982,003 issued Sept. 21, 1976 to Mitchell et al., and in U.S. Pat. No. 4,143,172, issued Mar. 6, 1979 to Mitchell et al. Another attempt at converting citrus waste to a food additive for human consumption is disclosed in U.S. Pat. No. 4,225,628, issued Sept. 30, 1980 to Lynn. According to the process described in this reference, citrus peel particles are de-watered by a process very similar to the lime de-watering process used in cattle feed production; the material is subsequently mixed with sesame grain flour, ground, dried and milled to a desired particle size. U.S. Pat. No. 4,379,782, issued Apr. 12, 1983 to Staub et al. discloses the use of citrus albedo or sugar beet pulp as a dietary fiber. The material is extracted with water or isopropanol to remove soluble carbohydrates and color and flavor materials. In spite of these attempts at finding more profitable uses for citrus waste, almost all of the citrus waste from juice canneries is still being converted in cattle feed and sold at a price which barely provides for recovery of the processing costs.

Sugar beet residue (commonly referred to as beet pulp), like citrus residue, is generally converted to cattle feed. As for citrus residues, attempts have been reported to convert beet pulp into a food additive suitable for human consumption. An example is Japanese Patent SHO 57-54573, publication date Apr. 1, 1982. This patent discloses a method for upgrading beet pulp by bleaching the pulp in hypochloric acid at pH 6.5 to 7.5, washing with water and drying. The material is reported to be capable of absorbing about 90% of its weight in water.

SUMMARY OF THE INVENTION

The present invention relates to vegetable absorbent material comprising: (a) from about 15% to about 80% pectin, having a degree of esterification of from about 1% to about 45% and less than about 50% of the pectin being in the form of a salt of a divalent cation; (b) from about 15% to about 80% of a material selected from the group consisting of cellulose, hemicellulose, lignin, and mixtures thereof; (c) from 0% to about 1% chloroform soluble lipids; and (d) from 0% to about 10% non-lipid organic materials extractable in a mixture of chloroform, methanol and water, said mixture having a volume ratio chloroform:methanol: water of 20:4:1; and (e) and 0% to about 6% water-soluble metal salts.

This invention further relates to a process for preparing an absorbent material from a pectin-containing vegetable material, comprising the steps of: (a) comminuting the vegetable material to an average particle size of from about 0.05 mm to about 3 mm; (b) de-esterifying the pectin to a degree of esterification of less than about 45%; (c) washing the vegetable material in soft water;

and (d) drying the vegetable material to a moisture content of less than 15%.

BRIEF DESCRIPTION OF THE DRAWING

FIG. 1 represents a flow chart of the analytical protocol used in characterizing the absorbent materials of the present invention.

DETAILED DESCRIPTION OF THE INVENTION

This invention relates to novel vegetable absorbent materials, a process for making the absorbent materials, and absorbent products comprising these novel absorbent materials.

This invention is based upon the discovery that pectin-containing vegetable materials can be converted into absorbent materials, using a relatively simple and inexpensive process. Pectin-containing vegetable materials which are suitable as starting materials for the production of the absorbent materials of the present invention contain at least about 15% pectin. Examples include apples, apricots, citrus peels, sugar beets and watermelon rinds. Zucchini for example, which has a pectin content of about 8%, is not suitable. Citrus peels and sugar beet pulp, each of which is a by-product of an important agricultural industry, are available in large quantities and at low cost and are therefore preferred starting materials for the preparation of the absorbent materials of the present invention.

The composition parameters of the vegetable starting materials and of the vegetable absorbent materials obtained upon processing have been determined in the comprehensive analytical protocol given below. Percentages of components of the materials, as used herein, are weight percentages as determined by this analytical protocol, except "equivalent percent divalent metals" and "degree of esterification", which are equivalent percentages of the total amount of polygalacturonic acid. Data obtained by a different analytical method, however, may differ, which precludes a direct comparison with such data. In particular the pectin, cellulose and hemicellulose contents and the degree of esterification which are determined indirectly, are parameters which are sensitive to the analytical method used.

In the analytical protocol the water content of a sample of the material to be analyzed is determined by Karl Fischer titration. The amounts of calcium, magnesium, sodium and potassium are determined by dry ashing followed by flame atomic absorption analysis of these metals. A third sample of the material is subjected to water extraction followed by a 40-hour Soxhlet extraction with chloroform. The amount of lipids in the extract is determined gravimetrically (hereinafter referred to as "chloroform soluble lipids"). If the material to be analyzed does not contain components which are both water-soluble and chloroform-soluble, the water extraction prior to the chloroform extraction may be omitted. Thus, it has been found that a chloroform extract of citrus peel derived absorbent materials does not contain watersoluble components, but that a sugar beet derived absorbent material does contain water-soluble components in the chloroform extract. A citrus peel-derived material may therefore be extracted with chloroform without prior water extraction, and an accurate reading of the amount of chloroform soluble lipids is obtained; a sugar beet derived material, on the other hand, must be extracted with water prior to chloroform extraction in order to obtain an accurate determination of the amount of chloroform soluble lipids.

A fourth sample is extracted with chloroform, and is subsequently subjected to a 40 hour Soxhlet extraction with chloroform/methanol/water (20/4/1, v/v/v). (If the determination of chloroform soluble lipids was made without prior water extraction the residue of that test can be used for this chloroform/ methanol/water extraction.) The amount of extracted material, which is determined gravimetrically, is the sum of the amounts of water-soluble metal salts and non-lipid organic materials. The metal cations are determined by flame ionization; the amount of water-soluble metal salts (hereinafter referred to as "watersoluble metal salts") is calculated therefrom using the molecular weight of the prevalent anion (which is known from the processing history of the sample; in case of chlorine bleaching, for example, the prevalent anion is chloride). The amount of nonlipid organic materials (hereinafter referred to as "non-lipid organic materials") is determined by subtracting the amount of water-soluble metal salts from the total amount of material extracted with the chloroform/methanol/water mixture.

The residue of the chloroform/methanol/water extraction contains cellulose, hemicellulose, lignin, pectin and pectates. The residue is split in four parts; one part is subjected to an acid hydrolysis of cellulose and hemicellulose, followed by GC analysis of the aldonitrileperacetate derivatives of the sugars. The second part of the residue is analyzed for protein; the protein content is calculated from the nitrogen value which is determined calorimetrically using the Nessler reagent. The third part of the residue is analyzed for lignin, using the gravimetrical method TAPPI T222-os-74. The fourth part of the residue is analyzed for calcium, magnesium, sodium and potassium by dry ashing followed by flame atomic absorption analysis of the metals. The amount of pectin is calculated from the total amount of bound metals (i.e., metals which cannot be removed by chloroform extraction or chloroform/methanol/water extraction) and the methoxy content. From the amounts of bound calcium and magnesium and the amount of pectin in the sample, the equivalent percent divalent metals is calculated as the equivalent percent of the polygalacturonic acid which is present as divalent metal salt. Likewise, the degree of esterification is calculated as the equivalent percent of the polygalacturonic acid which is present as the methyl ester, from the methoxy content and the total amount of pectin in the sample.

The analytical protocol is illustrated by the flow chart of FIG. 1. The water content 1 is determined by Karl Fischer titration. The methoxy content 2 is determined by base hydrolysis followed by GC analysis of the liberated methanol. Total metals 3 are determined by dry ashing followed by flame atomic absorption analysis of the metals. Lipids 4 are determined by gravimetry after a 40-hour Soxhlet extraction with chloroform. The residue of the chloroform extraction is then subjected to a 48-hour Soxhlet extraction with chloroform/methanol/water (20/4/1, v/v/v), other extractables 5 are determined gravimetrically. Lignin 6 is determined by gravimetry using TAPPI method T222-os-74. Protein 7 is calculated from the nitrogen value which is determined colorimetrically using the Nessler reagent. Cellulose and hemicellulose 8 are determined by acid hydrolysis followed by GC analysis of the aldononitrileperacetate derivatives of the sugars. Bound metals 12 are determined by dry ashing followed by flame atomic absorption analysis of the metals. Pectin 9 is calculated from the sum of the methoxy content 2 and bound metals 12. From bound calcium 12 and pectin 9 is calculated the equivalent percent calcium 11. From methoxy content 2 and pectin 9 is calculated the degree of esterification 10 as equivalent percent of polygalacturonic acid which is present as the methyl ester.

"Pectin", as determined by this method is the material in the composition which is capable of forming methyl esters or binding metals, calculated as polygalacturonic acid. The underlying assumptions are that the pectin does not contain any free acid groups, that all of the pectin is anhydrogalaturonic acid, and that no insoluble alkaline earth metal salts, other than calcium salts, are present. These assumptions have been verified by independent methods to be correct within a reasonable margin of confidence.

The sum of cellulose and hemicellulose is taken to be the total of neutral sugars left in the sample after the extractions with chloroform and the chloroform/methanol/water mixture. Cellulose may be determined separately as the total amount of glucose. The balance of neutral sugars is hemicellulose.

It has been discovered that the pectin in the composition plays an important part in determining the absorbent properties of the material. Although compositions differ among species and within species, more than 60% of the pectin in vegetable materials is generally present in the form of the methyl ester. In the case of organ peels, on the order of 20% is present as the calcium salt; the balance is generally in the protonated form, or an alkali metal salt, mostly potassium. The pectin in the absorbent materials of the present invention has a degree of esterification of less than about 45%. The vegetable starting material must therefore be subjected to a deesterification step which may be carried out by alkaline treatment of a pH of from about 8 to about 13, or by an enzyme such as pectin-esterase. The enzyme is naturally present in citrus peel.

Care should be taken that the amount of divalent metal pectates is not substantially increased. In particular, calcium pectates have been found to be detrimental to the absorption properties of the material. Moreover, the calcium pectates once formed cannot be readily converted to other pectic materials like alkali metal salts or pectic acids. In general, the total equivalent * of divalent metals must be less than 50%. The equivalent % of calcium is preferably less than 30%. In practical terms this means that calcium hydroxide or calcium carbonate cannot be used for alkaline deesterification. It is not necessary, however, to use distilled or deionized water: tap water has been found to not significantly reduce the absorbent properties of the materials, provided the water hardness does not exceed about 7 grains/gallon (corresponding to about 120 ppm $CaCO_3$) and provided that no excessive amounts of water are used. The term "soft water" as used herein therefore refers to water having a degree of hardness of less than 7 grains/gallon (less than about 120 ppm $CaCO_3$).

In particular when citrus waste is used, the vegetable starting material may contain complex mixtures of lipids and lipid-like materials, and other non-polymeric organic materials. The absorbent properties of the resulting absorbent material may be greatly enhanced by removing these organic extractable materials. It has been discovered that the organic extractables generally belong to one of two classes; a first class of materials which are soluble in chloroform and which have been identified as mostly non-polar lipids (these materials are referred to herein as "chloroform soluble lipids"); and a second class of materials which are not soluble in chloroform alone, but which are soluble in a mixture of chloroform, methanol and water (chloroform: methanol: water =20:3:1 (v/v/v)). This second class of materials is comprised of non-lipid organic materials and of water-soluble metal salts. The absorbent materials of the present invention may not contain more than about 1% chloroform soluble lipids, not more than about 10% non-lipid organic materials, and not more than about 6% water-soluble metal salts.

Hence, the present invention relates to vegetable absorbent materials comprising (a) from about 15% to about 60% pectin, said pectin having a degree of esterification of from about 1% to about 45%, and less than about 50% of the pectin being in the form of a divalent metal salt; (b) from about 15% to about 80% of a material selected from the group consisting of cellulose, hemicellulose, lignin and mixtures thereof; (c) from 0% to about 1% chloroform soluble lipids; (d) from 0% to about 10% non-lipid organic materials extractable in a mixture of chloroform, methanol and water, said mixture having a volume ratio chloroform:methanol:water of 20:4:1; and (e) from 0% to about 6% water-soluble metal salts.

Although the degree of esterification of the pectin does not appear to have a major effect on the ultimate absorption capacity of the absorbent material, low degrees of esterification are conducive to good wicking properties of the material. High wicking rates are important for a fast uptake of liquid. For use in absorbent products like disposable diapers, sanitary napkins and the like, good wicking properties of the absorbent material are highly desirable. The absorbent materials therefore must contain pectin which has a degree of esterification of less than about 45%, preferably less than about 20%.

The second major component of the absorbent material, next to pectin, is generally a mixture of cellulose, hemicellulose and lignin. The actual composition of this mixture is to a large extent determined by the choice of the raw material, and to a lesser extent by the process. For example, hemicellulose is likely to be partially removed during processing, which increases the relative amounts of cellulose and lignin in the mixture. Depending on the raw material source, the amount of lignin may be very small. For example, citrus waste has a much lower lignin level than beet pulp; yet very good absorbent materials can be prepared from either starting material.

It has been discovered that divalent metal pectates, in particular calcium pectates, are far inferior to alkali metal pectates (e.g. sodium pectates) with regard to absorbent properties. This is probably due to the fact that divalent metal salts of pectin are "cross-linked", whereby the divalent metal ion serves as the link between two adjacent pectin molecules. This crosslinking is believed to prevent swelling of the pectin and to thereby reduce its absorbency. Some of the pectin is naturally present as the calcium salt. Care must be taken not to increase the amount of calcium pectate any further. Therefore, during processing the materials should not be exposed to excessive amounts of calcium. If calcium is present in the form of an insoluble mineral salt which is not capable of interacting with the esterified pectin, the presence of calcium is probably not harmful at all.

One specific embodiment of this invention is a citrus peel-derived absorbent material comprising: (a) from about 30% to about 60% pectin, said pectin having a degree of esterification of less than about 20%, and less than about 30% of the pectin being in the form of a divalent metal salt; (b) from about 30% to about 60% of a mixture of cellulose and hemicellulose; (c) from 0% to about 1% chloroform soluble lipids; (d) from 0% to about 10% non-lipid organic materials extractable in a mixture of chloroform, methanol and water, said mixture having a volume ratio chloroform:methanol:water of 20:4:1; and (e) from 0% to about 6% water-soluble metal salts. Preferably, the peels of the ripe oranges or grapefruits are used as a starting material and the process is carried out in a way as to avoid excessive removal of hemicellulose.

A second specific embodiment of this invention is a sugar beet-derived absorbent material comprising: (a) from about 15% to about 35% pectin, said pectin having a degree of esterification of less than about 45% (preferably less than about 20%), and less than about 30% of the pectin being in the form of a divalent metal salt; (b) from about 20% to about 80% of a mixture of cellulose and hemicellulose; (c) from 0% to about 1% chloroform soluble lipids; (d) from 05 to about 10% non-lipid organic materials extractable in a mixture of chloroform, methanol and water, said mixture having a volume ratio chloroform:methanol:water of 20:4:1; and (3) from 0% to about 6% water-soluble metal salts.

Process

The process for preparing the vegetable absorbent material from the pectin-containing starting material depends to a large extent on the starting material being used. The process is aimed at reducing the degree of esterification of the pectin in the material, and removing excessive amounts of extractable materials. The process therefore comprises the steps of (1) comminuting a pectin-containing vegetable material to a particle size of from about 0.05 mm to about 3 mm; (b) de-esterifying the pectin to a degree of esterification of less than about 45%; (c) washing the vegetable material in soft water; and (d) drying the vegetable material to a moisture content of less than 15%.

The manner in which the deesterification is carried out is not critical and may, for example, be enzymatic or chemical.

Chemical deesterification of pectin may be carried out at acid or alkaline pH. Acid deesterification is not preferred as it is slow and leads to both divalent ion extraction and hemicellulose degradation. Alkaline deesterification is preferred but care must be exercised. Pectin methyl ester can degrade via a beta-elimination mechanism, so pH and temperature should be carefully controlled. Enzymatic deesterification may be carried out with the enzyme pectinesterase; this is particularly convenient when citrus peels are used as starting material because the enzyme pectinesterase is naturally present in citrus peels. Alternatively, deesterification may be carried out by soaking the vegetable material particles in a solution of an alkali metal hydroxide. The reaction rate increases with the concentration of hydroxyl ions, therefore the higher the pH, the faster the reaction will be. The pH should therefore be above about 8, preferably above about 9. Excessively high pH values tend to result in removal of hemicellulose and other desirable materials. Therefore, the pH should not exceed about 13, and preferably be below about 12. A degree of esterification of less than 45% is generally achieved after about 2 minutes at pH 9.5 or greater. As beta-elimination is very temperature dependent, a temperature of about 25° C. or lower is preferred. Prolonged contacting of the vegetable material with the alkali hydroxide solution results in a progressively lower degree of esterification of the pectin. It is generally not necessary to continue this deesterification step for more than about 2 hours, since little additional benefit is obtained by doing so.

The washing of the material is critical, since it is necessary to remove the alkaline material and excess soluble materials. Washing may be done with water or with an organic solvent. The latter has the advantage that chloroform-soluble lipids which may be present in the material are generally to some extent removed by an organic solvent like acetone, but not by a water wash. The washing step may be conveniently carried out as follows. Excess liquid is drained off from the reaction mixture of the deesterification step. Then, enough of the washing liquid (i.e. water or an organic solvent) is added in order to obtain a slurry with a solids content of about 2%. The slurry is equilibrated for about 5 to 15 minutes, and then the washing liquid is drained off. This washing step may be repeated. The number of washing steps is determined by the amount of contaminants in the starting material and the desired composition of the finished absorbent material. Typically, 2 or 3 washing steps will be necessary.

After excess washing liquid has been drained off after the last washing step, the liquid content of the remaining material is on the order of about 90%. This must be reduced to less than about 20% in order to obtain an absorbent material with optimum absorption properties. If an organic solvent is used in the washing step (e.g. acetone, isopropyl alcohol, or methanol), this solvent may be simply removed by evaporating it. The material may also be dried by solvent displacement: after the last washing step with water, the material is slurried up with an organic solvent like acetone or methanol, the solvent is then drained off and the excess is evaporated.

For economical reasons it may not be feasible to use any organic solvents in the process. In that case, water will have to be removed using a conventional drying technique. This may be either freeze drying, vacuum drying, or thermal drying. Of these three, freeze drying is the most attractive because it does not cause collapse of the fine capillaries which are naturally present in the material. Unfortunately, freeze drying is also the most expensive drying method of these three.

Thermal drying is economically the most attractive method of drying available. If the 90% moisture product from the washing step is dried in an oven, a board-like material is obtained which is not very absorbent. It has been discovered, however, that the material may be dried by spraying it into a counter current of superheated steam or heated air. The inlet temperature and the flow rate should be controlled as to result in an outlet temperature in the range of from about 60° C. to about 75° C. This results in a product which has a moisture content of less than 15%. Although thermally dried materials possess good absorption capacities, the absorption kinetics of such materials tend to be slow. The rate of absorption can be vastly improved by adding a surfactant to the slurry during the last washing step. An amount of surfactant of from about 1% to about 3% by weight of the amount of the slurry is generally sufficient. The type of surfactant is not critical. Examples of suitable surfactants are nonionic surfactants, e.g. ethoxylated fatty alcohols.

It is highly desirable to include in the process a bleaching step. Preferably, the bleaching is carried out with an oxidative bleaching agent. Examples of suitable bleaching agents are hydrogen peroxide, perborate, hypochlorite, chlorine dioxide and chlorine. Sodium hypochlorite is a preferred bleaching agent. For optimum properties of the absorbent material, and optimum safety of absorbent products made therewith, excess bleach and electrolytes introduced during the bleaching step will have to be removed. Bleaching is therefore best carried out prior to the washing steps. Since color compounds may be formed during alkaline deesterification, the bleaching step is best carried out subsequent to the deesterification step if alkaline deesterification is used (as opposed to enzymatic deesterification). In order to improve the effective use of the bleaching agent, it is desirable to include a washing step subsequent to the deesterification step and prior to the bleaching step, especially when citrus peels are the starting material. Hence, in case alkaline deesterification and bleaching are used, the process sequence is as follows: (a) communiting the pectin-containing vegetable material to a particle size of from about 0.05 mm to about 3 mm; (b) soaking the pectin-containing vegetable material particles obtained in step (a) in a solution of an alkali metal hydroxide in water at pH of from about 9 to about 12 and at a temperature of from about 15° C. to about 50° C., for a period of from about 2 minutes to about 120 minutes; (c) washing the product of step (b) in soft water; (d) bleaching the product of step (c) for from about 5 minutes to about 60 minutes; (e) washing the product of step (d) in soft water; and (f) drying the product of step (e).

The effect of bleaching is two fold. It removes color materials, thereby vastly improving the appearance of the absorbent material obtained by this process, and making it more suitable for use in consumer products like disposable diapers, sanitary napkins and the like. Bleaching further tends to decompose chloroform-soluble lipids into water-soluble fragments. Consequently, the bleaching step significantly reduces the level of chloroformsoluble materials in the finished product.

The removal of chloroform-soluble lipids is particularly important when citrus peels are used as the starting material. Citrus peels contain high levels of such chloroform-soluble lipids, and if water (as opposed to organic solvents) is used in the washing steps of the process, bleaching is instrumental in reducing the level of chloroform-soluble lipids to the desired level.

Although whole citrus peels may be used as the starting material, the flavedo part greatly increases the load of chloroform-soluble lipids and colored materials. It is therefore desirable to remove the flavedo part of the peel. The flavedo may be shaved off mechanically by machinery which is commercially available and designed for this purpose. Such equipment typically leaves about 30% of the flavedo on the albedo. It has been discovered that when these machine shaved peels are subjected to the process described hereinabove (including the bleaching step) an absorbent material is obtained which is negligibly less absorbent than the material obtained from an (handmade) all albedo starting material. Whole citrus peels may also be used as starting material. Highly acceptable absorbent materials may be made therefrom, albeit at the expense of a higher usage of bleaching chemicals.

Sugar beets, by their nature, contain only low levels of chloroform-soluble lipids. When processing sugar beet pulp, one may therefore forego the bleaching step is absorbent properties are the only concern. However, during alkaline deesterification, beet pulp develops a persistent green color and a bleaching step may be highly desirable or even necessary from an aesthetics viewpoint.

The processing of other pectin-containing raw materials will have become apparent from the foregoing. The bleaching step may be foregone if the starting material has a low chloroformsoluble lipid content, and contains little colored materials or if the aesthetics of the absorbent material are relatively unimportant (e.g. when intended for industrial use). The choice of the method of deesterification (enzymatic or alkaline treatment) is largely determined by economic determinations: enzymatic deesterification is relatively slow: alkaline treatment is faster and lends itself better to a continuous operation of the process. The choice of the washing liquid (water or an organic solvent) is likewise determined by economic considerations with which a person skilled in chemical engineering may be deemed well familiar.

Performance Testing

A. Partition Test

Samples of absorbent materials were subjected to a partitioning test, more fully described hereinbelow. This test has been designed to measure the absorption performance of the absorbent materials in competition with conventional cellulose fibrous webs, both under conditions of low liquid load and high liquid loads. The absorption fluid was "synthetic urine" (a solution of 1% NaCl, 0.06% $MgCl_2.6H_2O$ and 0.03% $CaCl_2.2H_2O$ in distilled water; the surface tension of the solution was adjusted to 45 dynes/cm with about 0.0025% of an octylphenoxy polyethoxy ethanol surfactant (Triton X-100, from Rohm and Haas Co.)). This test has been found to be predictive of the absorption capacity under typical usage conditions of absorbent materials when used as absorbent cores in diapers.

The partitioning tests were carried out as follows. A piece of polyethylene sheet (the kind of material generally used as a backsheet in disposable diapers) was placed on a flat, nonabsorbent surface. A round sample (57 mm diameter) of the absorbent material to be tested was placed on top of this backsheet. On top of that was placed a piece of paper tissue of the type generally used as envelope tissue in disposable diapers. On top of the envelope tissue was placed a sample of the reference material (southern soft wood slash pine fibrous web, 0.1 $g/cm^3$ density). Both sample and reference were prepared to have a weight as closely as possible approaching 0.6 g, corresponding to a basis weight of about 0.02 $g/cm^2$. The top sample was wetted with a predetermined amount (about 1 g) of synthetic urine, covered with another piece of backsheet, upon which a weight of 4.4 pounds (about 2 kg) was placed. This weight exerts a confining pressure of 1 psi (about $7 \times 10^3 N/m^2$) (when confined the samples have a diameter of about 60 mm). After five minutes equilibration time, the weight was removed and the two samples of absorbent material were weighed separately. To facilitate removal, a plastic mesh screen was placed in between the samples prior to the test. The "X-load", defined as the amount of synthetic urine (in grams) absorbed per gram of absorbent material was calculated for each sample. The sample was then placed back under the confining weight, and dosed with an additional dose of synthetic urine, equilibrated, and weighed. This was repeated several times (typically in the order of 8-10 times) so that the relative absorption performance of the test material over a wide range of X-loads was obtained as a function of the loading in the reference top layer.

B. Capillary Sorption Test

The absorption properties of absorbent materials were determined by their "synthetic urine" absorption and desorption behavior. The basic procedure and the design of the apparatus are described by Burgeni and Kapur, "Capillary Sorption Equilibria in Fiber Masses", *Textile Research Journal*, 37 (1967) 362, which publication is incorporated herein by reference. The test is particularly useful for determining absorption kinetics.

The absorption apparatus consisted of a horizontal capillary tube, approximately 120 cm long, connected by a valve to a fluid reservoir. The end of the tube was connected by tygon tubing to a glass funnel containing as ASTM 4-8 micron frit on which the absorbent material sample was placed under a confining pressure of 1 psi (about $7 \times 10^3 N/m^2$). The glass frit funnel was mounted on a vertical pole. The height of the frit above the capillary tube determined the hydrostatic suction being exerted on the sample. In a typical absorption/desorption experiment the volume of absorbed synthetic urine was determined as a function of hydrostatic suction, starting at 100 cm.

A simplified test was developed to determine the useful capacity of an absorbent web. In this test, the absorbed volume at −25 cm hydrostatic pressure was measured ("25 cm, Absorption"). Next, the frit containing the sample was lowered to zero hydrostatic pressure and the equilibrium value of sorbed volume measured ("0 cm, Void Volume"). Then the frit was raised again to the 25 cm mark and the absorbed volume at −25 cm in the desorption mode was determined ("25 cm, Desorption"). Readings of 25 cm absorption and 25 cm Desorption volumes were made after an equilibrium time of 20 minutes; readings of 0 cm Void Volumes were done after an equilibration time of 30 minutes.

Example One

Florida Valencia oranges juiced with an AMC Extractor were hand shaved to remove the flavedo and rag. The albedo was ground in an Urschel Grinder. Twenty-three pounds (about 10 kg) of the ground raw material, at 11.96% solids, was slurried in 75 pounds of water (about 34 kg), making a 2.8% solids slurry. The slurry was titrated to pH 9.5 and maintained at this pH by caustic addition for 30 minutes. The titration took 1.25 liters of 1N sodium hydroxide. The material was dewatered in a basket centrifuge. It was washed with 75 pounds (about 34 kg) of water while spinning in the centrifuge, and dewatered again. The 14.7 pounds (6.7 kg) of filter cake at 10.715 solids that resulted from this was slurried in 43 pounds (19.5 kg) of water, making 2.8% solids slurry. 3.8 liters of 5.15% sodium hypochlorite solution were added to the slurry and mixed for 15 minutes. The bleached material was dewatered in the centrifuge. It was washed again with 75 pounds (about 34 kg) of water while spinning and then dewatered. This resulted in 12.2 pounds (5.5 kg) of material at 10.3% solids for a yield of 45.7%.

The material was freeze-dried to a moisture content of about 10%. The chemical composition was determined by the analytical method described hereinabove.

The absorption properties were determined by the Capillary Sorption and Partition tests described hereinabove, and compared to those of conventional wood pulp fiber webs.

| A. GROSS CHEMICAL COMPOSITION | |
|---|---|
| Component | Coposition (% of dry weight) |
| Pectin | 44.0 |
| Other polymers | 52.7 |
| Chloroform soluble lipids | 0.70 |
| Non-lipid organics | 2.49 |
| Water-soluble metal salts | 0.13 |

| B. DISTRIBUTION OF PECTIN COMPONENTS | |
|---|---|
| Component | Equivalent % polygalacturonic acid |
| Methyl ester | 14.4 |
| Divalent metal salts | 29.8 |
| Monovalent metal salts | 55.8 |

| C. CAPILLARY SORPTION CAPACITY | | |
|---|---|---|
| | Capacity, ml Synthetic Urine/g Material, 1.0 psi | |
| Test Conditions | Reference Wood Pulp | Citrus Absorbent Material |
| 25 cm Absorb, 20 min | 1.9 | 8.4 |
| 0 cm Void Volume, 30 min | 4.5 | 9.4 |
| 25 cm Desorb, 20 min | 3.8 | 8.5 |

| D. PARTITION TEST | |
|---|---|
| Amount Absorbed, ml Synthetic Urine/g Material, 1.0 psi | |
| Reference Wood Pulp | Citrus Absorbent Material |
| 0.8 | 3.6 |
| 1.0 | 5.5 |
| 1.5 | 7.1 |
| 2.4 | 8.1 |
| 3.7 | 8.7 |
| 4.9 | 9.7 |

As the data indicate, a highly absorbent material was obtained. The absorbent properties of this material were far superior to those of a conventional wood pulp fiber web.

A second bath of citrus peel absorbent material is prepared by the same method. This batch is dried in a flash dry process, as follows. The filter cake obtained after the last centrifuge dewatering step is mixed in a 1% surfactant solution (Tergitol 15-S-9) to a 2.5% solids slurry. The slurry is mixed for 15 minutes. The material is dewatered in a basket centrifuge. The resulting filter cake is flash dried in two passes. On the first pass, the air inlet temperature is maintained between 150° C. and 200° C., and the air-flow is maintained so as to result in an outlet temperature between 60° C. and 65° C. On the second pass the inlet temperature is maintained between 90° C. and 125° C., and the outlet temperature between 50° C. and 55° C. A highly absorbent material is obtained.

Example Two

Four hundred thirty-four grams of finely ground sugar beet cattlefeed at 16.38% solids were slurried in 3 liters of water, making a 2.1% solids slurry. The slurry was titrated to pH 9.5 and maintained by caustic addition for 30 minutes. The titration took 12 ml of 1N sodium hydroxide. The material was dewatered in a basket centrifuge. It was washed with 50 pounds (22.7 kg) of water while spinning in the centrifuge, and then dewatered. The 462 grams of filter cake at 12.03% solids that resulted from this was slurried in 3 liters of water, making a 1.6% solids slurry. Five hundred ml of 5.25% sodium hypochlorite was added to this and it was mixed for 17 minutes. The bleached material was dewatered in the centrifuge. It was washed again with 50 pounds (22.7 kg) of water while spinning, and then dewatered. This resulted in 496 grams of material at 11.2% solids for a yield of 78%.

The material was freeze-dried to a moisture content of about 10%. The chemical composition was determined by the analytical method described hereinabove. The absorbent properties were determined by the Capillary Sorption and Partition Tests described hereinabove.

| A. GROSS CHEMICAL COMPOSITION | |
|---|---|
| Component | Composition (% of dry weight) |
| Pectin | 15.5 |
| Other polymers | 76.1 |
| Chloroform soluble lipids | 0.40 |
| Non-lipid organics | 6.79 |
| Water soluble metal salts | 1.60 |

| B. DISTRIBUTION OF PECTIN COMPONENTS | |
|---|---|
| Component | Equivalent % polygalacturonic acid |
| Methyl ester | 22.9 |
| Divalent metal salts | 25.4 |
| Monovalent metal salts | 51.7 |

| C. PARTITION TEST | |
|---|---|
| Amount Absorbed, ml Synthetic Urine/g Material, 1.0 psi | |
| Reference Wood Pulp | Sugar Beet Absorbent Material |
| 1.0 | 3.5 |
| 2.0 | 5.3 |
| 3.0 | 6.9 |
| 4.0 | 8.3 |
| 5.0 | 10.0 |

| D. CAPILLARY SORPTION CAPACITY | | |
|---|---|---|
| | Capacity, ml Synthetic Urine/g Material, 1.0 psi | |
| Test Conditions | Reference Wood Pulp | Sugar Beet Absorbent Material |
| 15 cm Absorb, 20 min | 1.9 | 6.3 |
| 0 cm Void Volume, 30 min | 4.5 | 7.9 |
| 25 cm Desorb, 20 min | 3.8 | 6.5 |

The data demonstrate that the material is highly absorbent.

Example Three

Five hundred grams of soaked, finely ground cattle feed (as used in the above Example Two) at 16.3% solids was mixed with 1.5 liters of a 5.2% solution of sodium hypochlorite (CLOROX, from Clorox Co., Oakland, CA) and 1.5 liters of distilled water and agitated for 15 minutes. It was deliquored in a basket centrifuge and washed with 30 liters of distilled water.

The material was freeze-dried to a moisture content of about 10%. The chemical composition was determined by the analytical method described hereinabove. The absorbent properties were determined by the Capillary Sorption and Partition Tests described hereinabove.

| A. GROSS CHEMICAL COMPOSITION | |
|---|---|
| Component | Composition (% of dry weight) |
| Pectin | 31.2 |
| Other polymers | 57.7 |
| Chloroform soluble lipids | 0.40 |
| Non-lipid organics | 10.3 |
| Water soluble metal salts | 0.85 |

| B. DISTRIBUTION OF PECTIN COMPONENTS | |
|---|---|
| Component | Equivalent % polygalacturonic acid |
| Methyl ester | 35.4 |
| Divalent metal salts | 18.4 |
| Monovalent metal salts | 46.2 |

| C. PARTITION TEST | |
|---|---|
| Amount Absorbed, ml Synthetic Urine/g Material, 1.0 psi | |
| Reference Wood Pulp | Sugar Beet Absorbent Material |
| 0.9 | 1.1 |
| 1.0 | 2.8 |
| 1.3 | 4.6 |
| 1.8 | 5.7 |
| 2.9 | 6.5 |
| 3.5 | 7.5 |
| 4.2 | 8.7 |

| D. CAPILLARY SORPTION CAPACITY | | |
|---|---|---|
| | Capacity, ml Synthetic Urine/g Material, 1.0 psi | |
| Test Conditions | Reference Wood Pulp | Sugar Beet Absorbent Material |
| 25 cm Absorb, 20 min | 1.9 | 6.2 |
| 0 cm Void Volume, 30 min | 4.5 | 7.2 |
| 25 cm Desorb, 20 min | 3.8 | 6.1 |

The data demonstrate that the material is highly absorbent.

Example Four

Two pounds (9.9 kg) of sugar beet cattle feed was soaked in 3 gallons (11 liters) of distilled water overnight at room temperature. The soaked feed was then coarsely chopped in a Waring blender and finely ground in an Urschel grinder. Enough distilled water was added to make a 1.5% solids slurry. To this slurry was added 300 ml of 1N NaOH over thirty minutes to maintain the slurry pH at 9.5. The material was then washed in a basket centrifuge while spinning with 24 gallons (91 liters) of distilled water. The washed cake was mixed with 5 gallons (19 liters) of a 5.2% solution of sodium hypochlorite (CLOROX, from Clorox Co., Oakland, CA) and 5 gallons (19 liters) of distilled water and mixed for 15 minutes. The bleached material was deliquored in the basket centrifuge for one minute and then washed with 3 gallons (11 liters) of distilled water while the centrifuge was still spinning. The washed cake was slurried in 3 gallons (11 liters) of water and deliquored in the centrifuge. This procedure was repeated twice.

The material was freeze-dried to a moisture content of about 10%. The chemical composition was determined by the analytical method described hereinabove. The absorbent properties were determined by the Capillary Sorption and Partition Tests described hereinabove.

| A. GROSS CHEMICAL COMPOSITION | |
|---|---|
| Component | Composition (% of dry weight) |
| Pectin | 24.7 |
| Other polymers | 66.0 |
| Chloroform soluble lipids | 0.40 |
| Non-lipid organics | 8.10 |
| Water soluble metal salts | 1.17 |

| B. DISTRIBUTION OF PECTIN COMPONENTS | |
|---|---|
| Component | Equivalent % polygalacturonic acid |
| Methyl ester | 16.9 |
| Divalent metal salts | 31.1 |
| Monovalent metal salts | 52.0 |

| C. PARTITION TEST Amount Absorbed, ml Synthetic Urine/g Material, 1.0 psi ||
| --- | --- |
| Reference Wood Pulp | Sugar Beet Absorbent Material |
| 0.9 | 1.0 |
| 1.2 | 2.7 |
| 1.7 | 4.4 |
| 2.3 | 5.5 |
| 3.4 | 6.3 |
| 4.4 | 7.3 |
| 4.6 | 8.3 |

| D. CAPILLARY SORPTION CAPACITY |||
| --- | --- | --- |
| | Capacity, ml Synthetic Urine/g Material, 1.0 psi ||
| Test Conditions | Reference Wood Pulp | Sugar Beet Absorbent Material |
| 25 cm Absorb, 20 min | 1.9 | 6.0 |
| 0 cm Void Volume, 30 min | 4.5 | 6.6 |
| 25 cm Desorb, 20 min | 3.8 | 6.2 |

The data demonstrate that the material is highly absorbent.

Example Five

A bath of Navel oranges were cut in half; the juice was extracted with a home juicer. The flavedo was removed using a Brown peel shaver. About 1200 grams of albedo was obtained, with some rag attached. The solids content of the sample was 11.5%.

The sample was mixed with 3.0 liters of distilled water in a large Waring Blender at the highest speed for two minutes. The mixture was allowed to stand for two hours, then dewatered over a Buchner funnel and washed with 6 liters of distilled water. The wet mass was put into a large container, and 3.8 liters of a 5.2% solution of sodium hypochlorite (CLOROX, from Clorox, Co., Oakland, CA) were added. The mixture was stirred rapidly for one hour at ambient temperature, then dewatered, and washed three times over a Buchner funnel. This yielded a mass of 590 g having a solids content of 7.5%. The material was freeze-dried.

Absorbency of the freeze dried material was measured using the Capillary Sorption Test described hereinabove with distilled water and with synthetic urine. Absorbency was also measured with the Partition Test described hereinabove.

| | Capacity, ml Synthetic Urine/g Material, 1.0 psi ||
| --- | --- | --- |
| Test Conditions | Reference Wood Pulp | Citrus Absorbent Material |
| 25 cm Absorb, 20 min | 1.9 | 6.0 |
| 0 cm Void Volume, 30 min | 4.5 | 7.6 |
| 25 cm Desorb, 20 min | 3.8 | 7.0 |

| | Capacity, ml Distilled Water/g Material, 1.0 psi ||
| --- | --- | --- |
| Test Conditions | Reference Wood Pulp | Citrus Absorbent Material |
| 25 cm Absorb, 20 min | 2.8 | 5.8 |
| 0 cm Void Volume, 30 min | 4.8 | 13.8 |
| 25 cm Desorb, 20 min | 3.6 | 12.1 |

| B. PARTITION TEST Amount Absorbed, ml Synthetic Urine/g Material, 1.0 psi ||
| --- | --- |
| Reference Wood Pulp | Citrus Absorbent Material |
| 1.0 | 3.3 |
| 2.0 | 5.5 |
| 3.0 | 6.4 |
| 4.0 | 7.2 |
| 5.0 | 8.1 |

Example Six

Hydrolysis Time Variations

Florida Valencia oranges juiced with an AMC extractor were machine shaved in a Brown peel shaver to remove approximately 70% of the flavedo and 90% of the rag. The shaved peels were ground in an Urschel grinder to a particle size of approximately 0.6 mm. Approximately 195 pounds (88.5 kg) of the Urschel ground peel at 12.2% solids were slurried in 380 pounds (172.5 kg) of distilled water making a 4.3% solids slurry. At this point a small batch was removed. This was the 0 minute exposure bath. While constantly agitating, the slurry was titrated to pH 9.8 and maintained at this pH by caustic addition. Small batches were removed at 30 and 120 minutes exposure time. Six normal hydrochloric acid was added to bring each caustic treated batch to pH 7. All three batches were dewatered in a basket centrifuge, washed and dewatered again. They were washed while spinning in a centrifuge with approximately 75 pounds (34 kg) of distilled water per 17 pounds (7.7 kg) of washed, dewatered filter cake. The filter cakes were added to enough 2.63% sodium hypochlorite bleach solution to make a 2.5% solids slurry. The slurries were agitated 18 minutes. The bleached materials were dewatered in a basket centrifuge, washed, and dewatered again. They were washed while spinning in the centrifuge with approximately 75 pounds (34 kg) of distilled water per 12 pounds (5.4 kg) of washed, dewatered filter cake. The bleached, washed materials were freeze dried to a moisture content of approximately 10%. The chemical composition was determined by the analytical method described hereinabove.

| A. GROSS CHEMICAL COMPOSITION ||||| 
| --- | --- | --- | --- | --- |
| | Composition (% of dry weight) ||||
| Component | Whole Peel Starting Material | 0 min | 30 min | 120 min |
| Pectin | 34.9 | 43.3 | 44.1 | 43.4 |
| Other polymers | 34.3 | 27.9 | 44.3 | 45.2 |
| Chloroform soluble lipids | 4.88 | 1.60 | 0.78 | 0.80 |
| Non-lipid organics | 25.0 | 17.7 | 6.81 | 6.99 |
| Water-soluble metal salts | 0.88 | 9.46 | 3.99 | 3.61 |

| B. DISTRIBUTION OF PECTIN COMPONENTS |||||
| --- | --- | --- | --- | --- |
| | Equivalent % polygalacturonic acid ||||
| Component | Whole Peel Starting Material | 0 min | 30 min | 120 min |
| Methyl ester | 59.8 | 50.7 | 17.7 | 5.3 |
| Divalent metal salts | 30.4 | 19.2 | 25.6 | 28.6 |
| Monovalent metal salts | 9.8 | 30.1 | 56.7 | 66.1 |

| C. CAPILLARY SORPTION CAPACITY ||||
| --- | --- | --- | --- |
| | Capacity, ml Synthetic Urine/g Material, 1.0 psi |||
| Test Conditions | 0 min | 30 min | 120 min |
| 25 cm Absorb, 20 min | 5.1 | 6.2 | 6.8 |
| 0 cm Void Volume, 30 min | 6.0 | 7.4 | 7.7 |
| 25 cm Desorb, 20 min | 5.2 | 6.7 | 6.9 |

| D. CAPILLARY SORPTION RATE |
| --- |
| 25 cm Absorption |

-continued

| | Rate, ml Synthetic Urine/g Material per minute, 1.0 psi | | |
|---|---|---|---|
| Measurement Time | 0 min | 30 min | 120 min |
| 15 sec | 1.4 | 1.7 | 3.1 |
| 30 sec | 2.2 | 2.9 | 5.2 |
| 45 sec | 2.8 | 4.0 | 6.0 |
| 1 min | 3.5 | 4.6 | 6.3 |
| 2 min | 5.0 | 5.6 | 6.6 |
| 10 min | 5.2 | 6.2 | 6.7 |

E. PARTITION TEST
Amount Absorbed, ml Synthetic Urine/g Material, 1.0 psi

| Reference Wood Pulp | Citrus Absorbent Material 0 Minute Sample |
|---|---|
| 1.1 | 1.1 |
| 1.5 | 2.7 |
| 2.3 | 4.2 |
| 3.8 | 4.8 |
| 4.8 | 5.9 |

Amount Absorbed, ml Synthetic Urine/g Material, 1.0 psi

| Reference Wood Pulp | Citrus Absorbent Material 30 Minute Sample |
|---|---|
| 0.9 | 1.3 |
| 1.1 | 3.2 |
| 1.4 | 5.0 |
| 2.0 | 6.4 |
| 3.3 | 7.2 |
| 4.3 | 8.0 |

Amount Absorbed, ml Synthetic Urine/g Material, 1.0 psi

| Reference Wood Pulp | Citrus Absorbent Material 120 Minute Sample |
|---|---|
| 0.9 | 1.2 |
| 1.0 | 3.4 |
| 1.2 | 5.0 |
| 2.0 | 6.4 |
| 3.3 | 7.3 |
| 4.4 | 8.0 |

The absorption properties were determined by the Capillary Sorption and Partition Tests described hereinabove.

The starting material (machine shaved orange peel) exceeded the limits set for chloroform soluble lipids, non-lipid organics and degree of esterification for absorbent materials of the present invention. The 0 min. sample, which is different from the starting material in that it has been bleached and washed, had a chloroform soluble lipids content within limits, probably due to the bleaching step. Hydrolysis with sodium hydroxide further improved the chemical composition of the material, resulting in a corresponding increase of the absorbent capacities. A low degree of esterification increased the sorption rate of the sample.

Example Seven

One batch of orange peels was converted to absorbent material, using the whole peel (i.e., no flavedo was shaved off), using the method described in Example Seven (hydrolysis time: 30 min., bleaching time: 18 min.). Another batch of the same orange peels was subjected to the process described in Example 7 of U.S. Pat. No. 3,982,003 (Mitchell) for the preparation of food thickeners (i.e., adjusting the pH to 8.5 with sodium carbonate, enzymatic hydrolysis for 18 hours, and subsequent dewatering and drying).

The citrus absorbent material prepared according to the present invention (CAM) was compared with the starting material and with the material prepared according to the Mitchell patent (Mitchell) for chemical composition and absorbent properties.

A. GROSS CHEMICAL COMPOSITION

| | Composition (% of dry weight) | | |
|---|---|---|---|
| Component | Whole Peel Starting Material | CAM | Mitchell |
| Pectin | 25.6 | 47.4 | 32.7 |
| Other polymers | 20.4 | 48.1 | 30.8 |
| Chloroform soluble lipids | 5.96 | 0.87 | 3.91 |
| Non-lipid organics | 46.2 | 3.18 | 30.7 |
| Water-soluble metal salts | 1.80 | 0.43 | 1.85 |

B. DISTRIBUTION OF PECTIN COMPONENTS

| | Equivalent % of the polygalacturonic acid | | |
|---|---|---|---|
| Component | Whole Peel Starting Material | CAM | Mitchell |
| Methyl ester | 59.5 | 7.2 | 14.1 |
| Divalent metal salts | 31.1 | 31.7 | 32.1 |
| Monovalent metal salts | 9.1 | 61.1 | 53.8 |

C. CAPILLARY SORPTION CAPACITY

| | Capacity, ml Synthetic Urine/g Material, 1.0 psi | |
|---|---|---|
| Test Conditions | CAM | Mitchell |
| 25 cm Absorb, 20 min | 6.6 | 1.9 |
| 0 cm Void Volume, 30 min | 8.2 | 4.4 |
| 25 cm Desorb, 20 min | 7.1 | 2.5 |

D. CAPILLARY SORPTION RATE

| | 25 cm Absorption Rate, ml Synthetic Urine/g Material/min., 1.0 psi | |
|---|---|---|
| Measurement Time | CAM | Mitchell |
| 15 sec | 1.9 | 0.1 |
| 30 sec | 3.1 | 0.2 |
| 45 sec | 4.1 | 0.3 |
| 1 min | 5.2 | 0.3 |
| 2 min | 6.1 | 0.6 |
| 10 min | 6.5 | 1.5 |

The process described in the Mitchell patent, although it effectively reduces the degree of esterification of the pectin, fails to remove enough of the chloroform soluble lipids or of the non-lipid organics. The resulting material is only poorly absorbent. The material of the present invention possesses excellent absorbent properties.

Example Eight

Calcium Hydroxide and Calcium Hypochlorite Treated Orange Peel Material

Florida Valencia oranges were juiced with an AMC Extractor and the peels were machine shaved with a Brown Peel Shaver so that approximately 70% of the flavedo and 90% of the rag was removed. This material was ground in an Urschel grinder to a particle size of about 0.6 mm. Twenty five pounds (about 11.3 kg) of the ground raw material at 12.4% solids, was slurried in 60 pounds (27.24 kg) of water, making a 3.4% solids slurry. The slurry was titrated to pH 9.5 and maintained at this pH by caustic addition for 30 minutes. The titration tool 1.10 liters of 1N calcium hydroxide. The material was dewatered in a basket centrifuge. It was washed with 75 pounds (about 34 kg) of water while spinning in the centrifuge, and dewatered again. The 12.5 pounds (5.6 kg) of filter cake was slurried in 65 pounds (29 kg) of water. 3.3 liters of 5.25% calcium hypochlorite bleach solution was added and the slurry was mixed for 18 minutes. The bleached material was dewatered in the centrifuge. It was washed again with 75 pounds (about 34 kg) of water while spinning and then dewatered. This resulted in 10 pounds (4.45 kg) of material at 14.06% solids.

The material was freeze dried to a moisture content of about 10%. The material was essentially hydrophobic.

This example illustrates the detrimental effect of calcium ions on the absorbent properties of the orange peel material.

Example Nine

Whole grapefruit peel was chopped into approximately ¼ to ⅜ inch (ca 6 mm×9 mm) cubes with a Fitzmill. The chopped peel was ground with an Urschel grinder. This ground peel was then chemically treated as follows:

680 pounds (about 308 kg) of ground peel was slurried in 2500 pounds (about 770 kg) of soft water in a 500 gallon (about 1800 l) vessel under strong agitation. To this slurry was added a sufficient quantity of 1 Normal sodium hydroxide to maintain the slurry pH between 9.0 and 9.5 for at least 20 minutes. This required about 4 gallons (about 14 liters). The slurry was then dewatered with a horizontal vacuum belt filter to 7-12% solids.

The resulting filter cake was reslurried in 2500 pounds (about 770 kg) of soft water, again in a 500 gallon (about 1800 l) tank under strong agitation. To this slurry was added 0.10 pounds (about 45 g) of sodium hypochlorite per pound of solids in the filter cake. The pH of the slurry was maintained at 9.0 to 11.0 by adding 1 Normal sodium hydroxide. About 3 gallons (about 11 l) was used. The slurry was maintained in contact with the hypochlorite for about 45 minutes and then dewatered again with a horizontal vacuum belt filter. During dewatering it was rinsed with 2500 to 5000 pounds (about 1135 kg to about 2270 kg) of water.

The resulting filter cake was again slurried in 1600 pounds (about 726 kg) of soft water in a 500 gallon (about 1800 l) tank under mild agitation. To this slurry was added 4 pounds (2.9 kg) of the nonionic surfactant Tergitol 15-S-9 (Union Carbide), which is a secondary alcohol ethoxylate. After 10 minutes of contact time, the slurry was once more dewatered with a horizontal vacuum belt filter, with no washing.

The resulting filter cake, containing 8.5% solids was flash dried in a 12-inch (30 cm) Barr & Murphy ring flash dryer to produce a granular powder, white to beige in color, containing 10% final moisture. Overall process yield from starting peel to final product was 45% on a solids basis.

| PARTITION TEST Amount Absorbed, ml Synthetic Urine/g Material, 1.0 psi | |
| --- | --- |
| Reference Wood Pulp | Grapefruit Absorbent Material |
| 1.0 | 2.2 |
| 2.0 | 5.0 |
| 3.0 | 6.2 |
| 4.0 | 7.0 |
| 5.0 | 7.9 |

These data demonstrate that the grapefruit absorbent material is high absorbent.

Example Ten

Red Delicious apples were peeled, quartered, and cored and then the pulp was processed in a disc shredder. One thousand grams of the shredded apple pulp, at 15.36% solids, was slurried in a solution of 4000 ml water and 25 ml 1N sodium hydroxide. The pH of the slurry, after adding the apple pulp, was 10.50. After eleven minutes the pH dropped to 7.45; an additional 11 mls of 1N sodium hydroxide was slowly added, bringing the slurry pH to 9.91. After a total time of thirty minutes, the slurry pH was 9.10. The material was dewatered in a basket centrifuge. It was washed with 25 kg of water while spinning in the centrifuge, and then dewatered. One hundred ninety-five grams of material at 8.11% solid was collected. One hundred and eighty-five grams of this material was reslurried in a solution of 3800 ml of water and 200 ml of 5.25% sodium hypochlorite solution, and mixed for eighteen minutes. The bleached material was dewatered in the centrifuge, then washed with 25 kg of water while spinning and then dewatered. The material was reslurried with 23 kg of water; then it was washed while spinning with 16 kg of water and dewatered. This resulted in 107.57 grams of material at 6.61% solids, yielding 4.63% of the initial shredded pulp solids. The material was freeze dried and its absorbent properties determined by the Partition Test.

| PARTITION TEST Amount Absorbed, ml Synthetic Urine/g Material, 1.0 psi | |
| --- | --- |
| Reference Wood Pulp | Apple Absorbent Material |
| 1.0 | 1.9 |
| 2.0 | 4.1 |
| 3.0 | 5.1 |
| 4.0 | 7.5 |
| 4.6 | 8.1 |

These data demonstrate that the material is highly absorbent.

Example Eleven

Sugar beet shreds were processed into an absorbent material as follows:

The shreds were soaked for one hour in soft water, then washed, then passed through a Sprout-Waldron disc refiner at a 2% consistency. After refining, the pH of the slurry was adjusted with sodium hydroxide to about 9.8, and maintained at this value for about 30 minutes. The slurry was then dewatered and washed with demineralized water, then slurried in a sodium hypochlorite solution (0.3 g $Cl_2$ per g solids at 2% consistency). The pH of the bleach solution was kept above 8.5 by adding small quantities of sodium hydroxide. The bleaching time was 54 minutes. After bleaching the pulp was washed with demineralized water, and passed through a Sprout-Waldron disc refiner. The material was washed four times with isopropyl alcohol (isopropanol), then dried in a forced air oven at 70° C.

The resulting material had a fibrous appearance, with fiber dimensions similar to those of a conventional hardwood pulp. Its absorbent properties were determined by the Partition Test.

| PARTITION TEST | |
|---|---|
| Amount Absorbed, ml Synthetic Urine/g Material, 1.0 psi | |
| Reference Wood Pulp | Sugar Beet Absorbent Material |
| 1.0 | 0.9 |
| 2.0 | 3.1 |
| 3.0 | 5.4 |
| 4.0 | 7.2 |
| 4.3 | 7.8 |

The above process was modified in that the washings with isopropyl alcohol were eliminated. Instead, the material was washed with soft water, then slurried at 2% consistency, in a 0.1% Tergitol solution, and flash dried. The resulting material was substantially similar to the material obtained after isopropyl alcohol treatment and oven-drying.

What is claimed is:

1. An absorbent material derived from a vegetable material containing at least about 15% pectin, said absorbent material comprising:
    (a) from about 15% to about 60% pectin, said pectin having a degree of esterification of from about 1% to about 45%, and from 18.5% to about 50% of the pectin being in the form of a divalent metal salt;
    (b) from about 15% to about 80% of a material selected from the group consisting of cellulose, hemicellulose, lignin and mixtures thereof;
    (c) from 0% to about 1% chloroform soluble lipids;
    (d) from 0% to about 10% non-lipid organic materials extractable in a mixture of chloroform, methanol and water, said mixture having a volume ratio chloroform:methanol:water of 20:4:1; and
    (e) from 0% to about 6% water-soluble metal salts.

2. A vegetable-derived absorbent material according to claim 1 wherein less than about 30% of the pectin is in the form of a calcium salt.

3. A vegetable-derived absorbent material according to claim 1 wherein the pectin has a degree of esterification of less than about 20%.

4. A vegetable-derived absorbent material according to claim 1 which is prepared from citrus peels, sugar beet pulp, apples, or mixtures thereof.

5. A citrus peel-derived absorbent material comprising:
    (a) from about 30% to about 60% pectin, said pectin having a degree of esterification of less than about 20%, and from 29.8% to about 30% of the pectin being in the form of a calcium salt;
    (b) from about 30% to about 60% of a mixture of cellulose and hemicellulose;
    (c) from 0% to about 1% chloroform soluble lipids;
    (d) from 0% to about 105 non-lipid organic materials extractable in a mixture of chloroform, methanol and water, said mixture having a volume ratio chloroform:methanol:water of 20:4:1; and
    (e) from 0% to about 6% water-soluble metal salts.

6. A sugar beet-derived absorbent material comprising:
    (a) from about 15% to about 35% pectin, said pectin having a degree of esterification of less than about 45%, and from 18.4% to about 30% of the pectin being in the form of a calcium salt;
    (b) from about 20% to about 80% of a mixture of cellulose and hemicellulose;
    (c) from 0% to about 1% chloroform soluble lipids;
    (d) from 0% to about 10% non-lipid organic materials extractable in a mixture of chloroform, methanol and water, said mixture having a volume ratio chloroform:methanol:water of 20:4:1; and
    (e) from 0% to about 6% water-soluble metal salts.

7. An absorbent material derived from a vegetable material containing at least about 15% pectin, said absorbent material comprising:
    (a) from about 15% to about 60% pectin, said pectin having a degree of esterification of from about 1% to about 45%, and less than about 50% of the pectin being in the form of a divalent metal salt, wherein the amount of divalent metal salt in the absorbent material is about the same as the amount naturally present in the vegetable material;
    (b) from about 15% to about 80% of a material selected from the group consisting of cellulose, hemicellulose, lignin and mixtures thereof;
    (c) from 0% to about 1% chloroform soluble lipids;
    (d) from 0% to about 10% non-lipid organic materials extractable in a mixture of chloroform, methanol and water, said mixture having a volume ratio chloroform:methanol:water of 20:4:1; and
    (e) from 0% to about 6% water-soluble metal salts.

8. A citrus peel-derived absorbent material comprising:
    (a) from about 30% to about 60% pectin, said pectin having a degree of esterification of less than about 20%, and less than about 30% of the pectin being in the form of a calcium salt, wherein the amount of calcium salt in the absorbent material is about the same as the amount naturally present in the citrus peel;
    (b) from about 30% to about 60% of a mixture of cellulose and hemicellulose;
    (c) from 0% to about 1% chloroform soluble lipids;
    (d) from 0% to about 10% non-lipid organic materials extractable in a mixture of chloroform, methanol and water, said mixture having a volume ratio chloroform:methanol:water of 20:4:1; and
    (e) from 0% to about 6% water-soluble metal salts.

9. A sugar beet-derived absorbent material comprising:
    (a) from about 15% to about 35% pectin, said pectin having a degree of esterification of less than about 45%, and less than about 30% of the pectin being in the form of a calcium salt, wherein the amount of calcium salt in the absorbent material is about the same as the amount naturally present in the sugar beet;
    (b) from about 20% to about 80% of a mixture of cellulose and hemicellulose;
    (c) from 0% to about 1% chloroform soluble lipids;
    (d) from 0% to about 10% non-lipid organic materials extractable in a mixture of chloroform, methanol and water, said mixture having a volume ratio chloroform:methanol:water of 20:4:1; and
    (e) from 0% to about 6% water-soluble metal salts.

* * * * *

UNITED STATES PATENT AND TRADEMARK OFFICE
CERTIFICATE OF CORRECTION

PATENT NO.   :   4,875,974
DATED        :   October 24, 1989
INVENTOR(S)  :   Thomas F. Rich It is certified that error appears in the above-identified patent and that said Letters Patent is hereby corrected as shown below:

At line 6 of Claim 1, change "18.5% to --18.4%--.

At line 10 of Claim 5, change "105" to --10%--.

Signed and Sealed this

Twenty-first Day of August, 1990

Attest:

HARRY F. MANBECK, JR.

*Attesting Officer*   *Commissioner of Patents and Trademarks*